United States Patent
Matsuura

(10) Patent No.: US 7,993,315 B2
(45) Date of Patent: Aug. 9, 2011

(54) SPERM COLLECTING APPARATUS

(75) Inventor: Tsutomu Matsuura, Tokyo (JP)

(73) Assignee: Tenga Co., Ltd., Nakano-Ku (JP)

( * ) Notice: Subject to any disclaimer, the term of this patent is extended or adjusted under 35 U.S.C. 154(b) by 1033 days.

(21) Appl. No.: 11/881,750

(22) Filed: Jul. 27, 2007

(65) Prior Publication Data
US 2008/0004577 A1    Jan. 3, 2008

(30) Foreign Application Priority Data

Jun. 8, 2005  (JP) .................................. 2005-168908
Jun. 1, 2006  (WO) .................. PCT/JP2006/310969

(51) Int. Cl.
*A61F 5/44*    (2006.01)
*A61F 5/00*    (2006.01)

(52) U.S. Cl. .......................................... 604/349; 600/38
(58) Field of Classification Search .......... 604/349–353; 600/38–41; 435/325, 363, 366, 374
See application file for complete search history.

(56) References Cited

U.S. PATENT DOCUMENTS

| 5,782,818 A | * | 7/1998 | Shubin | .......................... 604/349 |
| 5,807,360 A | | 9/1998 | Shubin | |
| 5,885,233 A | * | 3/1999 | Adachi | .......................... 601/138 |

FOREIGN PATENT DOCUMENTS

| JP | 10-099361 A | | 4/1998 |
| JP | 3076183 | * | 9/2000 |
| JP | 3076183 U | | 12/2000 |
| JP | 3076627 U | | 1/2001 |

* cited by examiner

*Primary Examiner* — Leslie R Deak
*Assistant Examiner* — Philip R Wiest
(74) *Attorney, Agent, or Firm* — Masuvalley & Partners

(57) ABSTRACT

A sperm collecting apparatus is provided and includes a container including a cylindrical container main unit that has an opening portion on at least one end face in a longitudinal direction thereof and a cap that is attached to and detached from the opening portion of the container main unit to close and open the opening portion, and a core member which is accommodated in said container and has an insertion room extending from an insertion port at one end face in a longitudinal direction therein. The core member includes a core main unit having said insertion port and the insertion room and a plurality of ribs provided upright from an outer face of the core main unit to cross one another, and sealed rooms are formed through the outer face of the core main unit.

6 Claims, 7 Drawing Sheets

(a)

(b)

(a)

(b)

(c)

(a)

(b)

SPERM COLLECTING APPARATUS

TECHNICAL FIELD

The present invention relates to a sperm collecting apparatus, and in particular relates to an improvement of conventionally-used sperm collecting apparatuses based on social demands, such as medical researches, demands for medical treatment, prevention of sex-related crimes, antiprostitution activities, and prevention of spreading of venereal diseases, and the like.

BACKGROUND OF THE INVENTION

Various sperm collecting apparatuses for collecting men's sperm have been proposed for the necessities of medical research or treatment. For example, a sperm collecting apparatus is used for medical needs such as examination of sexual function of a husband from the sperm collected for examination of the cause of marital infertility, or treatment of sexual dysfunction, reservation and storage of the sperm for artificial insemination. Simple sperm collecting apparatuses that can be conventionally available at a low price and that do not cause sanitary or health problems due to the disposability thereof have been known, and they can satisfy various social needs, such as prevention of sex-related crimes, antiprostitution activities, and a decrease of the number of infected persons of venereal diseases, by satisfying individual sexual desires.

For example, Japanese Utility Model Registration No. 3076627 has proposed a sperm collecting apparatus where an interior member made from a gel-like synthetic resin (styrene block copolymer (styrene thermoplastic elastomer)) having a deep recessed space inside is provided in a cylindrical container main unit, a plurality of small projections projecting to the recessed space and fold-shaped portions are provided inside the interior member, and an exterior member made from urethane resin is provided so as to cover the circumference of the interior member.

In the sperm collecting apparatus, one end of the cylindrical container main unit whose upper and lower faces are flat is opened, an assembly obtained by assembling the exterior member to the interior member so as to cover the circumference thereof is inserted into the container from the opening, an insertion port of the interior member positioned on the side of the opening of the container is closed by a disk-like sponge lid, and the opening of the container is then sealed by a cap. A cross-shaped cut is preliminarily formed at a central portion of the sponge lid so that a penis can be inserted into the interior member via the sponge lid by causing the cut to communicate with the insertion port of the interior member.

Since the conventional container main unit has a structure that requires an exterior member made from urethane resin, there are various problems such that productivity lowers due to the number of assembling steps caused by an increased number of parts and an amount of waste when the sperm collecting apparatus is discarded increases.

The container is formed in a cylindrical member having a diameter (about 5 to 6.5 cm) equal over its entire length using plastic having a required hardness and thickness. Accordingly, there is a tendency that pressure applied to a penis inside the insertion member from an inner wall of the container main unit through the exterior member becomes approximately uniform during an operation for penis rubbing so that stimulations to the penis are simplified. Particularly, since expansion of the interior member is restricted by the exterior member, there is a tendency that stimulations caused by pressure become excessively strong. As a result, when an elderly person, a disabled person or the like who does not wish for strong stimulations as compared with a healthy young male using such a sperm collecting apparatus, there is often a case that pain increases due to excessively strong stimulations, and a sperm collection purpose cannot be achieved. That is, it is difficult to adjust stimulations according to individual reaction or liking. On the contrary, there is a limitation for a user who does not respond to an ordinary stimulation to obtain stronger stimulations corresponding to his liking in view of the structure of the container.

Since the recessed space in the interior member is sealed except for the insertion port, when a user inserts his penis into the recessed space from the insertion port, a space is formed between the interior member inner wall and his penis, the degree of tight contact between the both tends to lower. Particularly, since air tends to be easily accumulated between the most sensitive penis distal end and a depth portion of the recessed space, a problem occurs that accumulated air cannot be discharged even if any strong rubbing action is repeated and sufficient stimulations required for ejaculation cannot be obtained. Even if degassing is tried with strong grasp of the container main unit, since a distance between the inner wall of the container main unit having an equal diameter over its entire length (namely, a cylindrical shape) and the interior member inside the container main unit is about 2 cm, application of sufficient and appropriate pressure cannot be conducted and it is impossible to conduct degassing without imparting pain to a penis.

Since the container has a cylindrical shape with a diameter equal over its entire length, the exterior member covering the circumference of the interior member has a cylindrical shape similar to the container, and the inner wall of the exterior member has a straight shape that does not include any undulation, so that a force for retaining and shape-holding the interior member disposed inside the exterior member cannot be developed sufficiently, deformation of the interior member inside the exterior member becomes free beyond necessity, and buckling or deformation of the interior member tends to occur, so that normal use becomes difficult when the buckling occurs.

Since an elastomer that configures the interior member is expensive, it is effective for total cost reduction to thin the thickness of the interior member in order to reduce material cost, but when the thickness of the interior member is thinned, the interior member tends to buckle at a time of insertion or a rubbing operation of a penis, which can result in an unusable state. When securing of a shape-holding performance is tried in order to solve the problem by covering a periphery of the interior member with the exterior member, there is another problem of an increased number of assembling steps, which is a drawback caused by an increased number of parts.

A proper amount of lubricating liquid (lotion) is also charged in the recessed space for improving a lubricating property between the inner wall of the recessed space of the interior member made from an elastomer and a penis, but when the collecting apparatus is placed upright such that the cap side of the cylindrical container main unit faces downwardly during transportation, storage and display of the collecting apparatus, the insertion port side of the interior member always faces downwardly so that much lubricating liquid passes through the cut of the sponge lid and accumulates on the opening side of the container main unit, or inside the cap. In this state, when the cap is detached, lubricating liquid spills out from the opening of the container to the outside to drop on an outer face of the container or adhere on a hand or cloths of a user, thereby causing discomfort or causing a state that an amount of lubricating liquid in the recessed space of the interior member becomes insufficient during actual use.

In order to deal with such a drawback, it is necessary to store or display a collecting apparatus having a configuration in a state that a container thereof is disposed upright such that a bottom portion thereof opposed to an opening portion of a container main unit faces downwardly, but when the container is placed upright such that the opening portion faces upwardly, lubricating liquid accumulates in only the inner bottom portion (depth portion) of the recessed space of the interior member, so that lubricating liquid at an inlet (insertion port) of the recessed space and the inner wall is put in a dried state, which can obstruct penis insertion, can cause buckling or deformation of the interior member due to an excessive increase of frictional resistance between a penis and the inner wall of the recessed space, or can cause injury of the penis.

Conventionally, since a peripheral edge of the opening portion of the container main unit repeatedly abuts on a proximal portion of a user's penis or skin around his penis during use, there can be a drawback that such portions are injured or discomfort is given to the user.

SUMMARY OF THE INVENTION

The present invention has been achieved in view of these circumstances and one object thereof is to prevent a reduction of productivity and increase of waste due to an increased number of assembling steps, which is a drawback caused by interposing a urethane plate between a container and a core member (an interior member).

Another object is to prevent excessive stimulations or simplification of stimulations during an operation for penis rubbing to achieve a sperm collection purpose by applying optimal and necessary and sufficient stimulations suitable for such a user, even when not only a healthy person but also an elderly person, a disabled person or the like who is susceptible to stimulations as compared with a healthy young male using such a collecting apparatus, and to further achieve a use purpose of a user who requires stimulations stronger than stimulations required for an ordinary user.

Particularly, another object is to adjust pressure applied to a penis inside the container main unit to fluctuate stimulations by devising a shape of the core member while using a container with a simple shape.

Furthermore, another object is to conduct degassing without delay at a time of insertion and rubbing of a penis in order to eliminate the drawback due to air accumulating between a distal end of the penis and the inner depth portion of the core member when the penis is forcibly inserted into the core member made from gel-like resin in the container, rubbing between the distal end of the penis and the inner wall of the core member becomes insufficient in a rubbing operation performed thereafter so that stimulations required for erection and ejaculation cannot be obtained.

Further, another object is to eliminate a drawback such that the core member tends to be buckled or deformed at a time of insertion or rubbing of a penis and normal use becomes difficult when buckling is caused.

Further, another object is to provide a sperm collecting apparatus which can prevent lubricating liquid (lotion) charged in the core member from leaking from the insertion port of the core member at an opening time of a cap even if the sperm collecting apparatus unused is placed upright with the opening side of the container facing downwardly such that the lubricating liquid accumulates at the inlet side of the core member while the collecting apparatus unused is being stored or displayed.

Further, another object is to eliminate the drawback that due to repetitive abutting of a peripheral edge of the opening portion of the container main unit on a proximal portion of a user's penis or skin around his penis during use of the container main unit, a body portion of the user on which the peripheral edge abuts is injured or the user feels discomfort.

By utilizing air pressure inside a closed space as a pressure source serving as a source imparting stimulations or tightening forces to a penis instead of the conventional urethane-made exterior member, varied stimulations or tightening can be achieved. That is, a user can arbitrarily conduct pressure adjustment or fluctuation so as to satisfy his liking during use based on utilization of air pressure.

In order to achieve the above object, the invention is a sperm collecting apparatus including: a container including a cylindrical container main unit whose at least one end face in a longitudinal direction is opened and a cap that is attached to and detached from an opening portion of the container main unit to close and open the opening portion; and a core member made from gel-like resin, which is accommodated in the container and has an insertion room extending from an insertion port at one end face in a longitudinal direction therein, characterized in that the core member includes a core main unit having the insertion port and the insertion room and a plurality of ribs provided upright from an outer face of the core main unit to cross one another, and sealed rooms are formed by the outer face of the core main unit, the plurality of ribs, and the inner wall of the container main unit according to a contact of outer end edges of the respective ribs with the inner wall of the container main unit.

Thereby, a buffering portion, an elastic portion, or a reaction portion based on air in a plurality of sealed spaces arranged in an axial direction and a circumferential direction is formed so that tightening pressure is generated.

Another embodiment of the invention is characterized in that, in the invention according to claim 1, the ribs include a plurality of plate-like lateral ribs extending in a direction crossing an axial direction of the core main unit and a plurality of longitudinal ribs extending in a direction parallel to the axial direction of the core main unit and connecting the respective said lateral ribs.

Another feature of the invention includes a lid plate tightly contacting with the core member to close the insertion port of the core member is disposed at the insertion port of the core member.

Another feature of the invention includes a sponge lid having a cut line is interposed between an end face of the core member on the insertion port side and the cap where a portion of the sponge lid is caused to project beyond an end edge of the opening portion of the container main unit to the outside.

In addition, the cut line for degassing serving as a check valve is formed at a proper portion in a distal end portion of the core member.

The invention also includes a bottom portion sponge layer is interposed between an inner bottom face of the container main unit and a distal end face of the core member.

The invention also includes a small-diameter portion is provided on at least one portion of an outer peripheral face of the container main unit.

The invention may also include an inner cap having a projecting portion which is fitted in the insertion port of the core main unit from the outside to close the insertion port and a supporting face which supports the projecting portion and contacts with one end face of the core main unit in the longitudinal direction.

The invention may also include a space for accumulating lotion is formed between the supporting face of the inner cap and one end face of the core main unit in the longitudinal direction.

The invention may also include a flange portion formed on one end face of the core main unit in the longitudinal direction, an outer peripheral edge of the flange portion bulges beyond the opening portion of the container main unit, and the outer peripheral edge of the flange portion is kept in an outwardly-folded state such that the outer peripheral edge of the flange portion covers an end edge of the opening portion of the container main unit.

Also, the core member may have a reversed structure where two sides of the core member are reversed.

The invention may also include a tightening member that may be elastically attachably and detachably provided on an outer face of the core member.

According to the present invention, since any other member is not interposed between the container and the core member, the number of parts can be reduced, and improvement in productivity and a reduction of the amount of waste by simplification of the assembling step can be achieved.

On the other hand, in view of the necessity for blocking excessive expansion of the core main unit after a penis has been inserted into the insertion recess, it is necessary to impart a pressurizing force (an expansion-restricting force in an outer diametrical direction) into an inner diametrical direction to an outer peripheral face of the core main unit. In the present invention, however, since the longitudinal and lateral ribs provided upright on the outer peripheral face of the core main unit form the airtight rooms between the ribs and the inner face of the container, a drawback such that stimulations and pressurizing forces to the lower penis due to excessive expansion of the core main unit in the outer diametrical direction at a time of insertion and rubbing operation of a penis can be prevented owing to an air cushion based on elastic forces of the ribs and the airtight rooms.

When the conventional core member is covered with the exterior member made from urethane, since the exterior member is collapsed during use, which results in difficulty in returns to an original shape, the pressurizing force lowers. In the present invention, however, since the pressurizing structure utilizing air is adopted, pressure does not lower. Even if pressure in the airtight rooms once lowers, the air is recharged during repetition of a rubbing operation so that the internal pressure is raised.

It is preferable that the contact state between the longitudinal and lateral ribs and the inner face of the container is a tightly contacting state, and at least one portion of the contact portion therebetween can be put in a bonded state. Although the entire contact portion can be put in a bonded state, such a merit can be achieved by leaving a non-contact portion that air leakage from respective airtight rooms occurs during a rubbing operation, thereby changing an internal pressure.

Furthermore, since the outer peripheral face of the core member is not restricted by the urethane plate rigidly, which is different from the conventional example, expansion of the core member in the container in the diametrical direction can be made possible to a certain extent, so that excessive load on a penis is cancelled. Particularly, the plurality of sealed spaces are formed between the outer face of the core member and the inner wall of the container by the ribs provided on the core member made from an elastomer, and an occurrence of excessive tightening to a penis is prevented by utilizing a cushioning function of the sealed spaces, so that a soft feeling can be obtained during a rubbing operation. A portion of air leaks in each rubbing operation, which results in a change of pressure and stimulations. Since pressure and stimulations change for each of insertion and removal, fluctuating stimulations can be provided. Pressure, vacuum, and a tightly contacting feeling can be arbitrarily adjusted.

Further, by performing a rubbing operation and simultaneously performing an operation for opening and closing the small hole provided at a proper portion on the container with a user's finger, pressure acting on his penis can be adjusted so that stimulations can be varied.

Therefore, even if not only a healthy person but also an elderly person, a disabled person or the like who is susceptible to stimulations as compared with a healthy young male using such a collecting apparatus, a sperm collection purpose can be achieved by applying minimal stimulations for the user.

By providing the cut line serving as a check valve in a distal end portion of the core member, air that tends to be accumulated inside the core member can be removed without delay at a time of insertion and rubbing of a penis. As a result, the contact is made tighter, so that a sperm collecting effect is improved.

Further, since the unused collecting apparatus is disposed upright with the opening side of the container facing downwardly such that the lubricating liquid (lotion) accumulates on the core member inlet side when the unused collecting apparatus is stored or displayed, it is made possible to insert his penis smoothly as it is when the cap is opened and the lubricating liquid is prevented from leaking from the insertion port of the core member.

Further, it is able to eliminate the drawback that due to repetitive abutting of a peripheral edge of an opening portion of the container main unit on a proximal portion of a user's penis or skin around his penis during use of the container main unit, a body portion of the user on which the peripheral edge abuts is damaged or the user feels discomfort.

Further, since the intermediate portion of the container is formed in a small diameter so that movement or deformation of the core member inside the container can be prevented, buckling of the core member can be prevented and a positioning easiness can be improved.

Since the inner cap having a projecting portion which is fitted in the insertion port of the core member from the outside to close the insertion port and a supporting face which supports the projecting portion and contacts with one end face of the core member in the longitudinal direction is provided, leakage of lotion from the insertion port can be prevented. By providing a space for accumulation of lotion for insertion between the inner cap and the front end face of the core main unit, smoothness at a time of insertion can be secured. Since an outer peripheral edge of the flange portion formed on an one end face of the core member in the longitudinal direction bulges beyond the opening portion of the container main unit in an outer diametrical direction and the outer peripheral edge of the flange portion is kept in an outwardly-folded state, and end edge of the opening portion of the container main unit is not exposed and it is covered with the soft flange. Such a state that a portion of a human body directly rubs on the end edge of the opening portion to cause pain during usage is prevented.

Since the core member includes a reversed configuration such that two sides of the core main unit are reversed, longitudinal and lateral ribs serve as folds projecting from the inner wall of the insertion port in their curved state, stimulations at a time of penis insertion can be further improved.

EXPLANATION OF THE CODES

1 Sperm collecting apparatus, 2 Container, 3 Container main unit, 4 Opening portion, 4a End edge, 5 Cap, 10 Core member, 11 Insertion port, 12 Insertion room, 20 Sponge layer, 30 Sponge member (Bottom sponge layer), 35 Lid plate, 40 Sponge lid, 41 Cut line, 50 Core main unit, 51 Rib, 51a Lateral rib, 51b Longitudinal rib, 55 Flange portion, 55a Outer peripheral edge, 60 Inner cap, 61 Projecting portion, 62 Supporting face, 70 Tightening member, 71 Clamping piece, 72 Elastic strap.

DETAILED DESCRIPTION OF THE PREFERRED EMBODIMENTS

Figure 1:
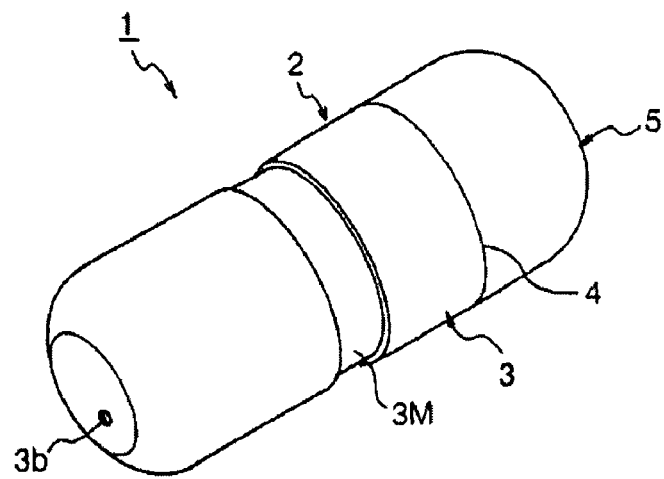
FIG. 1 is an appearance perspective view of a sperm collecting apparatus according to one embodiment of the present invention.
Figure 2:
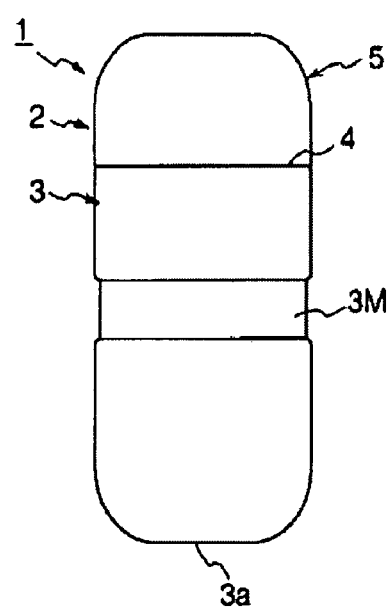
FIGS. 2(a) and 2(b) are a front view of the sperm collecting apparatus and a bottom view thereof.
Figure 2:
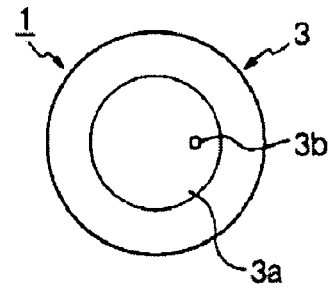
Figure 3:
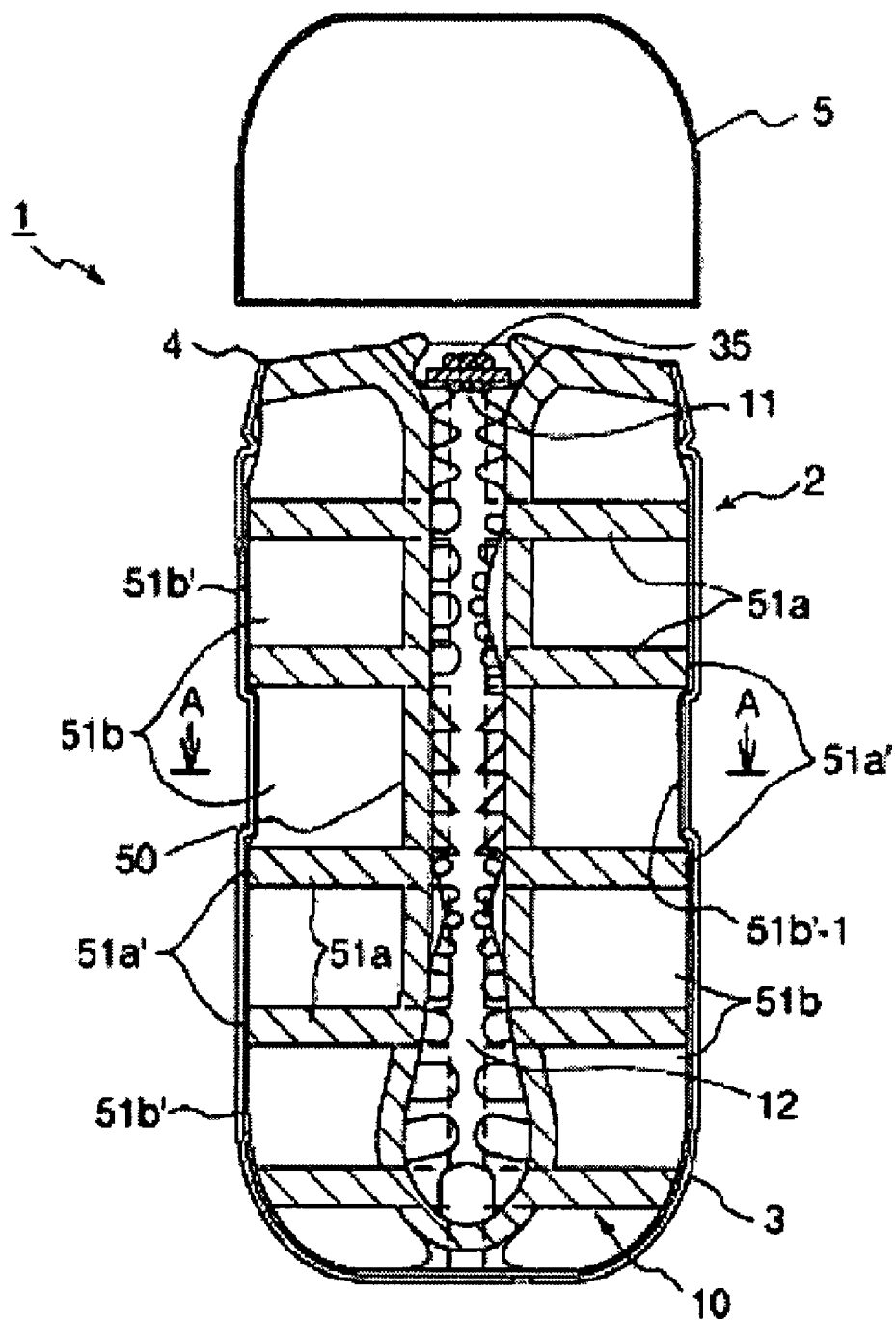
FIG. 3 is a vertical sectional view of the sperm collecting apparatus.
Figure 4:
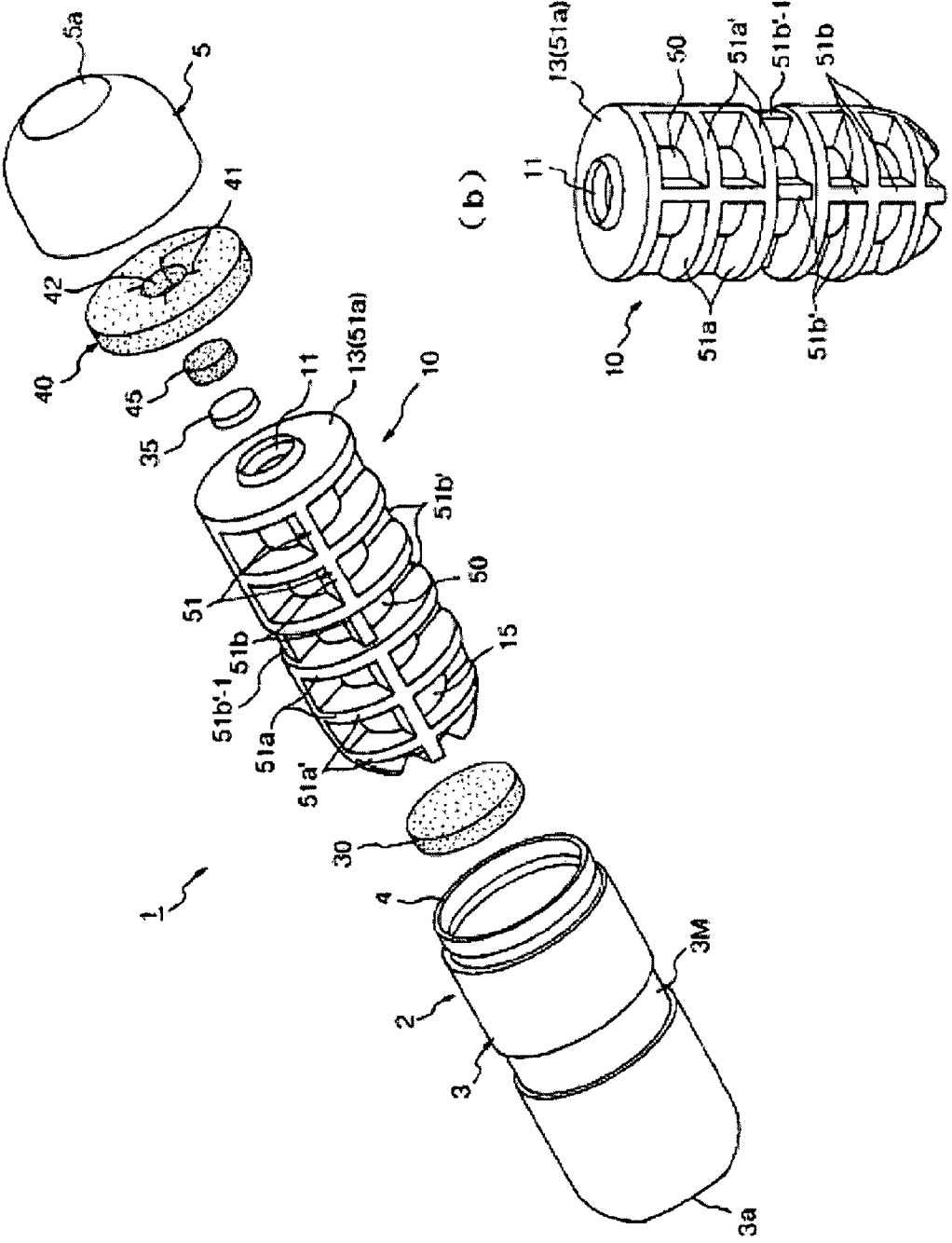
FIGS. 4(a) and 4(b) are an exploded perspective view of respective constituent elements and an appearance perspective view of a core member.
Figure 5:
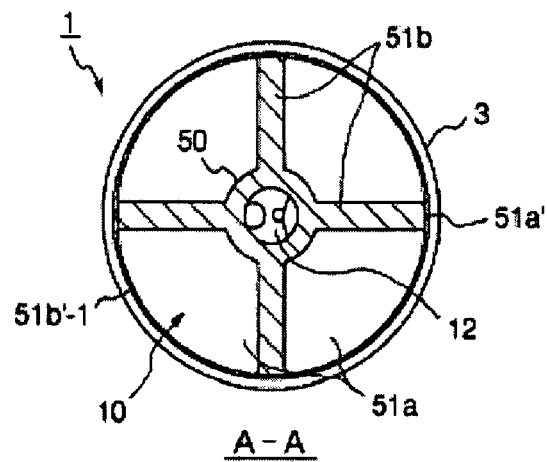
FIG. 5 is a sectional view of line A-A in FIG. 3.

FIG. 1 is an appearance perspective view of a sperm collecting apparatus according to one embodiment of the present invention, FIGS. 2(a) and 2(b) are a front view of the sperm collecting apparatus and a bottom view thereof, FIG. 3 is a vertical sectional view of the sperm collecting apparatus, FIGS. 4(a) and 4(b) are an exploded perspective view of respective constituent elements and an appearance perspective view of a core member, and FIG. 5 is a sectional view of the sperm collecting apparatus taken along line A-A in FIG. 3.

The sperm collecting apparatus 1 includes a container 2 having container main unit 3 whose one end in a longitudinal direction is opened thereof and which has a small-diameter portion 3M at a proper portion (an intermediate portion) on an outer peripheral face, and a cap 5 that is attached to and detached from an opening portion 4 of the container main unit 3 to close and open the opening portion, and a core member 10 made from a gel-like resin, that is accommodated in the container main unit 3 and has an insertion room 12 extending from an insertion port 11 at one end face in a longitudinal direction therein.

The sperm collecting apparatus 1 can additionally include a sponge member (a bottom sponge layer) 30 disposed on an inner bottom face of the container main unit 3, a lid plate 35 additionally provided to the insertion port 11 of the core member 10 to close the same, and a sponge lid 40 additionally provided on an end face of the core member 10 at an insertion side thereof and tightly contacts with the inner wall of the container main unit 3 to perform such a function as positioning of the core member for fixing thereof, according to necessity.

The container main unit 3 is formed from a resin material with a required thickness and it is a non-cylindrical member having the intermediate portion (the small diameter portion) 3M with an outer diameter smaller than those at both end portions thereof at the longitudinal direction, and an upper face 5a of the cap 5 made of a similar resin material is a flat face suitable for stationary placement on a flat face. Accordingly, since the container main unit 3 closed by the cap 5 can be placed upright on a flat face such that the upper face 5a of the cap 5 faces downwardly, such a drawback that lubricating liquid accommodates in a depth portion of the insertion room 12 and lubricating liquid at the inlet side runs dry is eliminated.

A small hole 3b for degassing is preliminarily formed at the other end 3a of the container main unit as necessary and it is preliminarily sealed in the unused state by a seal (not shown). The seal is removed when it is used and the degree of tight contact or feeling of close contact (tight-fitting feeling or feeling of being sucked) between the inner wall of the core member and a user's penis can be adjusted by opening and closing the small hole 3b during use with his finger. That is, since his penis tightly contacts with the inner wall of the core member in a state that the small hole 3b is closed, a tightening force becomes strong, while the tightening force becomes weak in a state that the small hole 3b is opened. It is made possible to fluctuate a tightening force (a pressure difference between an inner pressure and the atmospheric pressure) to fluctuate stimulations according to a simple operation such as only opening and closing the small hole 3b. When the user feels pain in his penis, he can open the small hole 3b.

The core member 10 is a bag member made from gel-like resin with viscosity such as an elastomer or gel-like rubber, it includes a large-diameter flange (rib) 13 at an end face on the insertion side, and the insertion room 12 with a diameter larger than that of the insertion port is formed inside the small-diameter insertion portion 11 so as to communicate therewith. A projection(s) or a fold(s) is formed in the insertion room 12 with a proper arrangement. Lotion or the like serving as lubricating liquid is preliminarily charged in the insertion room 12 with a proper amount.

The core member 10 has the following characteristic configuration. That is, the core member 10 includes a core main unit 50 having the insertion hole 11 and the insertion room 12, and a plurality of ribs 51 provided upright on an outer face of the core main unit 50 to cross each other, and outer end edges of respective ribs 51 contact with an inner wall of the container main unit 3 so that sealed rooms S are formed by the outer face of the core main unit, the plurality of ribs 51 and the inner wall of the container main unit.

In this embodiment, the ribs 51 includes a plurality of plate-shaped (flange-like) lateral ribs 51a (including the flange 13) and a plurality of longitudinal ribs 51b extending in a direction parallel to an axial direction of the core main unit 50 and connecting respective said lateral ribs 51a.

A shape and a thickness of each lateral rib 51a are set such that the rib tightly contacts with the inner wall of the cylindrical container main unit at an outer end edge 51a' thereof.

The longitudinal rib 51b is formed such that an outer end edge 51b' tightly contacts with the inner wall of the container main unit. Since the container main unit 3 has the small diameter portion 3M, an outer end edge 51b'-1 of the longitudinal rib 51b corresponding to the small diameter portion 3M is formed to have a small diameter (an outer peripheral edge is notched). Since a stepped portion is also formed at a periphery of the opening portion 4 to which the cap 5 is attached, a stepped portion is formed at a distal end portion of the longitudinal rib 51b so as to correspond to the former stepped portion.

An outer end edge of each rib may not tightly contact with the inner wall of the container main unit in a state that a penis is not inserted into the insertion recess 12, and the outer end edge of the rib can tightly contact with the inner wall of the container main unit to form the sealed rooms S simultaneously with expansion of the core member due to penis insertion.

Since this configuration is adopted, when the core member 10 is inserted into the container main unit 3, a plurality of sealed rooms S arranged in longitudinal and lateral directions can be formed by the outer face of the core main unit, the plurality of ribs 51, and the inner wall of the container main unit. Respective portions configuring the core member 10 made from gel-like resin themselves have elastic forces, while a function serving as an air cushion is added owing to presence of the sealed rooms S.

Since the outer end edges 51b'-1 of some of the longitudinal ribs 51b of the core member 10 are notched and an inner wall (an inwardly-projecting portion) of the small-diameter portion 3M of the container main unit is fitted into the notched portions, a shape-holding force of the core member is raised, so that buckling of the core member is prevented at a time of insertion or rubbing of a penis.

The concept of the term "tight contact" used in case of tight contact between the rib and the inner wall of the container main unit includes not only tight contact due to viscosity of the rib but also bonding utilizing adhesive. The rib can be entirely or partially bonded to the inner wall of the container main unit or it can be caused to contact therewith in a non-bonded state.

A short cut line 15 for degassing serving as a check valve is formed by providing a cut at a proper point on a distal end portion of the core member 10 in advance. Since the cut line 15 is completely closed in a non-insertion state of a penis according to an elastic force of the core member itself, lubricating liquid inside the core member is prevented from leaking and when an internal pressure is raised due to penis insertion, air that tends to be accommodated between a penis distal end and an inner bottom face of the insertion room 12 can be degassed by opening the cut line 15. After the air is removed, even if an operation for rubbing of the penis is performed, the cut line 15 continues to close so that lubricating liquid hardly flows to the outside. However, even if a small amount of lubricating liquid inside the core member leaks from the cut line 15, there will not be such a state that lubricating liquid inside the core member lacks to such an extent that the shortage disturbs use of this apparatus.

By arranging a lid plate 35 that tightly contact with an end face of the core member around a peripheral edge of the insertion port 11 to openably/closably close the insertion port at the insertion port 11 of the core member 10 to close the insertion portion, lubricating liquid charge in the insertion room 12 is prevented. Accordingly, even if the container 2 is placed such that the cap 5 side faces downwardly, lubricating liquid does not leak, so that the insertion port side of the insertion room 12 can be maintained in a sufficiently-lubricated state. Reduction of lubricating liquid inside the core member due to drying is prevented owing to presence of the lid plate 35. Drying inside the core member is further prevented by impregnation of lubricating liquid in the sponge lid 40. Since the lid plate 35 is made from gel-like resin equal to the material for the core member 10, it tightly contacts with the insertion side end face of the core member 10 to tightly close the insertion port 11. On the other hand, when a user inserts his penis into the insertion port 11, the lid plate 35 is pushed into the inner portion of the insertion port 11 by a distal end of his penis, so that it does not interfere with a rubbing operation performed thereafter. That is, irregular stimulations can be imparted to his penis, which leads to improvement of a sperm collecting efficiency.

A cut line 41 for penis insertion is formed in the sponge lid 40 additionally provided on a face of the flange 13 of the core member 10 in advance, but when the insertion port 11 is closed from the outside using the lid plate 35, a hole 42 fitted with the lid plate 35 can be formed at a central portion of the sponge lid 40 in advance. Thereby, an inside face of the sponge lid 40 can be caused to tightly contact with the face of the flange 13, so that a force for positioning and fixing the core member 10 is increased by the sponge lid 40. A force for fixing the lid plate 35 is also increased.

The lid plate 35 is pushed into the insertion room 12 at a time of penis insertion to be interposed between a distal end of the penis and the inner wall of the insertion room 12, so that it can apply irregular stimulations to the distal end of the penis according to rolling of the lid plate 35 or the like.

When the sponge lid 40 having the cut line 41 is interposed between the end face of the core member 10 on the insertion port and the cap 5, a portion of the sponge lid 40 is protruded beyond the opening portion end edge of the container main unit 3 to the outside by a predetermined amount (for example, 3 mm to 5 mm). By adopting this configuration, a drawback such that due to repetitive abutting of an opening portion peripheral edge of the container main unit 3 on a proximal portion of a user's penis or a skin around his penis during use of the container main unit 3, a body portion of the user on which the opening portion peripheral edge abuts is damaged or the user feels discomfort about the use can be eliminated.

A sponge member (a bottom sponge layer) 30 as another member is additionally provided at a distal end of the core member 10. Since a sponge material which can be elastically shrunk is disposed between the distal end of the core member 10 and the inner bottom face of the container main unit 3, it is possible to accommodate a long or short penis length. That is, when a penis length is shorter than a standard length, the sponge positioned at the distal end side of the core member 10 receives the distal end of the core member to prevent collapse and deformation of a distal end shape of the core member 10 and maintains a rubbing force to a penis distal end, while when the penis length is longer than the standard length, the sponge positioned at the distal end side of the core member 10 is compressed and deformed by the penis distal end to be capable of maintaining the rubbing force between the distal end of the core member 10 and the penis distal end.

In addition, a rib or a projection (a cushion damper) can be provided without use of the sponge member 30 so as to project from the distal end of the core member 10 to produce a damping function between the inner depth wall of the container and the penis.

When a user uses this sperm collecting apparatus, he detaches the cap 5 to insert his penis. Since the core main unit 50 expands due to penis insertion so that the outer end edges of the respective longitudinal and lateral ribs tightly contact (are pressure-contacted) with the inner wall of the container main unit 3, a plurality of sealed rooms S are formed by the respective longitudinal and lateral ribs, the outer wall of the core main unit 50, and the inner wall of the container main unit 3. Since the sealed rooms are uniformly formed over the whole outer face of the core main unit 50, they can be caused to uniformly function as an air cushion with respect to the whole outer face. Accordingly, while stimulations and pressurizing due to excessive expansion of the core main unit 50 are prevented from lowering, excessive stimulations and pressurizing forces can be prevented from occurring. Elastic pressure and tightening provides a tight contact feeling to a user.

By performing an operation in penis rubbing while closing the small hole 3b provided in the container main unit 3 with a user's finger, an internal pressure in the container main unit 3 is raised so that a pressurizing feeling and a vacuuming feeling can be obtained. When rubbing is performed in a state that the small hole 3b is opened, a different feeling can be obtained.

Alternatively, stimulations fluctuate due to pressure leakage even in a state that the hole is not closed.

That is, since pressure adjustment is performed according to a difference between the state that the small hole has been closed and the state that it is not closed, the feeling obtained at a time of insertion and rubbing of a penis becomes different, so that the sense of satisfaction can be achieved.

Next, FIGS. 6(a), 6(b) and 6(c) are a perspective view showing a configuration of an inner cap used in a sperm collecting apparatus according to another embodiment of the present invention, a vertical sectional view showing main parts of the sperm collecting apparatus before the inner cap is attached, and a vertical sectional view of main parts showing an attached state of the inner cap. Like portions as those in the sperm collecting apparatus according to the respective embodiments described above are attached with like reference numerals in the following explanation.

The sperm collecting apparatus 1 according to this embodiment includes an inner cap 60 having a projecting portion 61 that is fitted to an insertion port 11 provided in a front end face of the core main unit 50 from the outside to close the insertion port 11 and a supporting face (a supporting plate) 62 that supports the projecting portion 61 and contacts with one end face (a front end face) of the core main unit 50 in a longitudinal direction thereof. The inner cap 60 is made from of, for example, a resin plate (a material harder than a constituent material for the core main unit or the sponge) thinner than the container main unit 3, and the projecting portion 61 is pressure-fitted into the insertion portion 11 so that the projecting portion 61 is caused to tightly contact with an inner peripheral face of the insertion port 11 to prevent leakage of lotion inside the core main unit. Since the projecting portion 61 is harder than a constituent material for the core main unit, it tightly contacts with and is fitted into the insertion port 11 to be capable of preventing leakage of lotion and attaching and detaching operations to and from the insertion port 11 can be performed smoothly. The supporting face 62 expanding from an outer peripheral edge of the projecting portion 61 in an outer diametrical direction tightly contacts with at least one portion of the front end face of the core main unit 50 to serve to prevent the spread or outflow of lotion in the outer diametrical direction even if the lotion leaks. Since an outer peripheral edge of the supporting face 62 tightly contacts with (or is preliminarily integrated with) an inner peripheral face of the cap 5, the whole inner cap 60 is pressure-contacted with the front end face of the core main unit 50, when the cap 5 is closed, so that positional deviation is prevented and lotion leakage is not occurred.

An annular recess 62a is provided on the supporting face 62 of the inner cap 60 and a recess 55A is provided on the front end face (the flange portion) 55 of the core main unit 50 so that the recess 62a faces, so that lotion for insertion is held between both the recesses 62a and 55A. By adopting this configuration, a state that a sufficient amount of lotion has adhered on an outside peripheral face of the insertion port 11 can be secured when the inner cap 60 is detached prior to use. Therefore, when a user inserts his penis, he can perform smooth insertion without feeling discomfort. On the other hand, lotion for insertion can be retained in a space formed between the recesses 62a and 55A without leakage at a closed time of the cap 5. Accordingly, lotion is prevented from leaking from the front end face of the core main unit and drying during transportation and display.

On the other hand, the insertion port is conventionally capped by causing disk-like urethane foam including an X-shaped cut at a central portion thereof to abut on the front end face of the core main unit, but since sealing obtained by the cutting is insufficient, such a problem as leakage of lotion during usage or dry (occurrence of pain at a time of penis insertion) due to leakage of lotion during transportation or display arises.

According to the present embodiment, these drawbacks can be eliminated once for all. Particularly, since no urethane is present on the insertion port side, a user does not feel rough textured discomfort at his insertion and feels smooth and comfortable.

Figure 7:
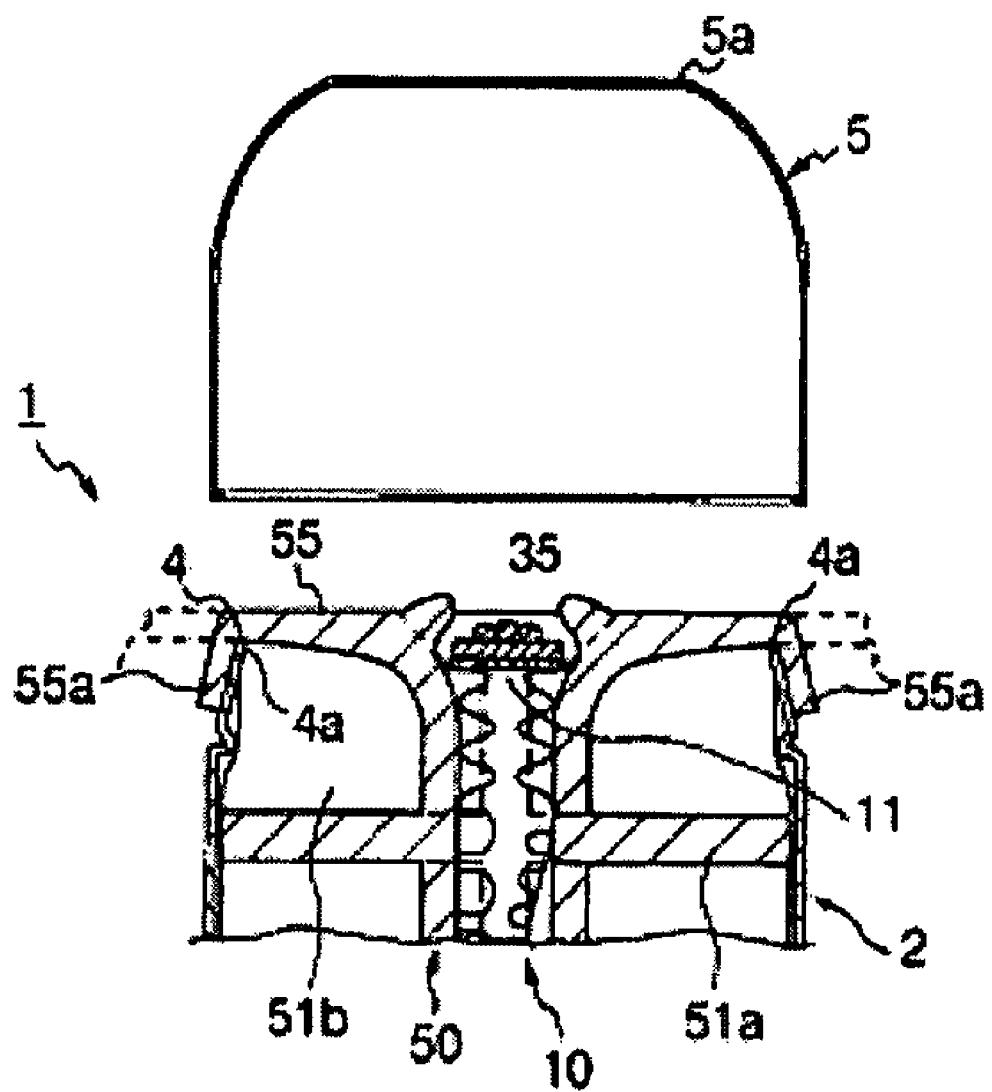
FIG. 7 is a vertical sectional view showing a configuration of main parts of a sperm collecting apparatus according to another embodiment of the present invention.

Next, FIG. 7 is a vertical sectional view showing a configuration of main parts of a sperm collecting apparatus according to another embodiment of the present invention. In the sperm collecting apparatus according to this embodiment, a disk-like flange portion (a front end face) 55 is formed on one end face of the core main unit 50 in a longitudinal direction (an axial direction), an outer peripheral edge 55a of the flange portion 55 made from a soft material is formed to have a large diameter so as to bulge beyond the opening portion 4 of the container main unit 3 in an outer diametrical direction, and an end edge 4a of the opening portion 4 of the container main unit 3 is covered with the outer peripheral edge 55a of the flange portion 55 made from a soft material so that the outer peripheral edge of the flange portion 55 is held in a state that it has been folded outside the opening portion 4 such that a portion of a human body does not contact with the end edge 4a directly. The outer peripheral edge 55a of the flange portion 55 is preferably bonded to the outer face of the opening portion 4 in a state that it has been pushed back to the outside of the opening portion 4.

Alternatively, by adopting a structure that the outer peripheral edge 55a of the flange portion 55 can be caused to elastically contact with the outer face of the opening portion 4 in a state that it has been folded back in advance, the folded-back state can be maintained without using adhesive.

Alternatively, after the outer peripheral edge 55a of the flange portion 55 is folded back to the outer face of the opening portion 4, it can be pressed on the outer face of the opening portion 4 using a pressing member made from a cylindrical member (a circular member) (not shown).

With this configuration, when a user detaches the cap 5 to expose the front end face of the core main unit 50 and inserts his penis into the insertion port 11 to conduct a rubbing operation of his penis, he is prevented from feeling pain due to contact of the end edge 4a of the opening portion 4 with his lower abdomen. The outer peripheral edge 55a is prevented from being peeled off during usage by bonding the outer peripheral edge 55a of the folded flange portion to the outer face of the opening portion 4 in advance.

Figure 6:
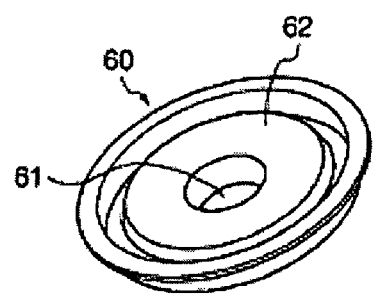
FIGS. 6(a), 6(b) and 6(c) are a perspective view showing a configuration of an inner cap used in a sperm collecting apparatus according to another embodiment of the present invention, a vertical sectional view showing main parts of the sperm collecting apparatus before the inner cap is attached, and a vertical sectional view of main parts showing an attached state of the inner cap.
Figure 6:
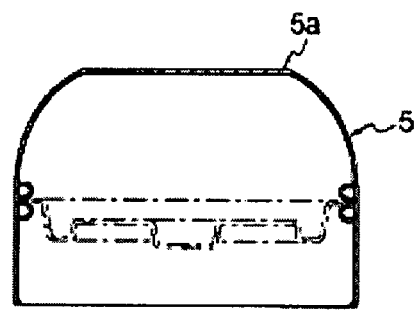
Figure 6:
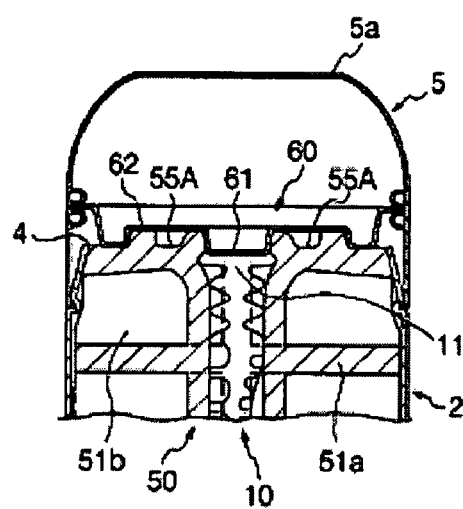
Figure 6:
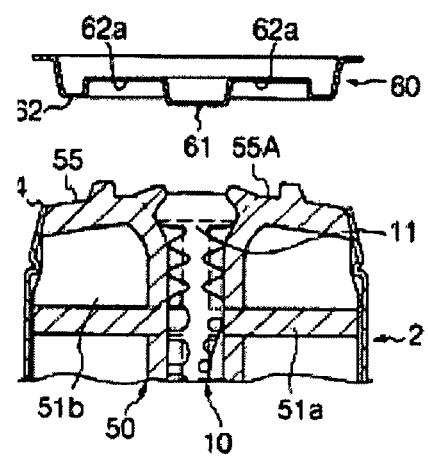

The configuration of the flange portion according to this embodiment and the inner cap according to the embodiment shown in FIG. 6 can be combined.

FIGS. 8(a) to 8(d) are explanatory diagrams showing a modification procedure of a sperm collecting apparatus according to a modified embodiment of the present invention.

A feature of the sperm collecting apparatus according to this embodiment lies in a configuration that reversing is performed such that two sides of the core member 10 according to each embodiment turns back. That is, in order to obtain a configuration that the inner wall of the insertion room 12 forms an outer wall of the core member 10 and the outer wall of the core member 10 forms an inner wall of the insertion room 12 by reversing the cover member 10 shown in FIG. 8(a), after the bottom portion of the core member 10 is pushed into the insertion room 12 so that the bottom portion projects from the insertion port 11 to the outside, as shown in FIG. 8(b), the bottom portion is further pulled out from the insertion port 11 completely, so that the core member 10 where the inner wall face of the insertion room 12 has been exposed to the outside can be obtained, as shown in FIGS. 8(c) and 8(d). At this time, a state that the ribs 51 (the lateral ribs 51a and the longitudinal ribs 51b) have projected inside the inner peripheral face of the insertion port 11 can be obtained. Particularly, the lateral rib 51a positioned at the uppermost portion is put in a curved state like a flower petal, as shown in FIG. 8(d). These ribs 51 are pressure-contacted with one another by a strong force so that stimulations at a time of insertion or rubbing of a penis can be improved.

As explained in this embodiment, it is made possible to utilize the plurality of ribs provided upright on the outer face of the core main unit 50 for forming the sealed rooms between the ribs and the inner wall of the container main unit 3 as means for imparting stimulations to a penis by reversing the core member 10.

Since the ribs 51 projecting inside the insertion port 11 are pressure-contacted with one another so that the insertion port 11 is elastically sealed, leakage of lotion can be prevented. Since it does not appear that the core member 10 takes a hole, the core member can demonstrate a novel image visually. Since the insertion port 11 is elastically sealed by the ribs, a user can obtain a binding feeling (an air cushion effect) owing to air pressure (or fluctuation of air pressure) sealed inside the core member when he inserts his penis while expanding the ribs.

The core member 10 having the reversed structure can be manufactured by manufacturing the core member of each of the embodiments to reverse the same. However, by manufacturing a mold with a structure that a core member having a reversed structure can be injection-molded in advance, a core member having a reversed structure can be manufactured directly using the mold.

When a core member 10 with a non-reversed structure is manufactured by injection molding using a mold, it is necessary for forming projections or folds inside the insertion room 12 to conduct a molding procedure of resin injection, resin hardening, mold opening, and mold releasing in a state that a core pin including recesses on an outer face corresponding to the projections or the folds is disposed in a cavity in the mold. Therefore, since a resin material corresponding to the projections or the folds enters in the recesses on the outer face of the core pin, such a resin material disturbs drawing-out of the core pin, which results in a deterioration of workability.

On the other hand, when a core member with a reversed structure is manufactured by manufacturing a core member 10 with a non-reversed structure according to injection molding using a mold to reverse the core member, it is unnecessary to use a core pin including recesses as a core pin used at an injection molding. That is, since an inner wall corresponding to the insertion room 12 of the core member before being reversed configures an outer face of the core member when the core member is used in its reversed state, it is unnecessary to provide projections or folds in advance. Accordingly, productivity can be enhanced according to improvement of workability for drawing-out of the core pin, so that cost reduction can be realized.

The core member 10 of a reversed type whose outer side has been wound with a plate member made from urethane foam can be accommodated in the container main unit 3. With this configuration, a tightening feeling based on pressure from the urethane foam can be obtained. Buckling of the core member during use can be prevented by holding the projections provided on the outer face of the core member 10 by means of notches provided at portions of the urethane foam to prevent positional deviation between the core member and the urethane foam.

Figure 8:
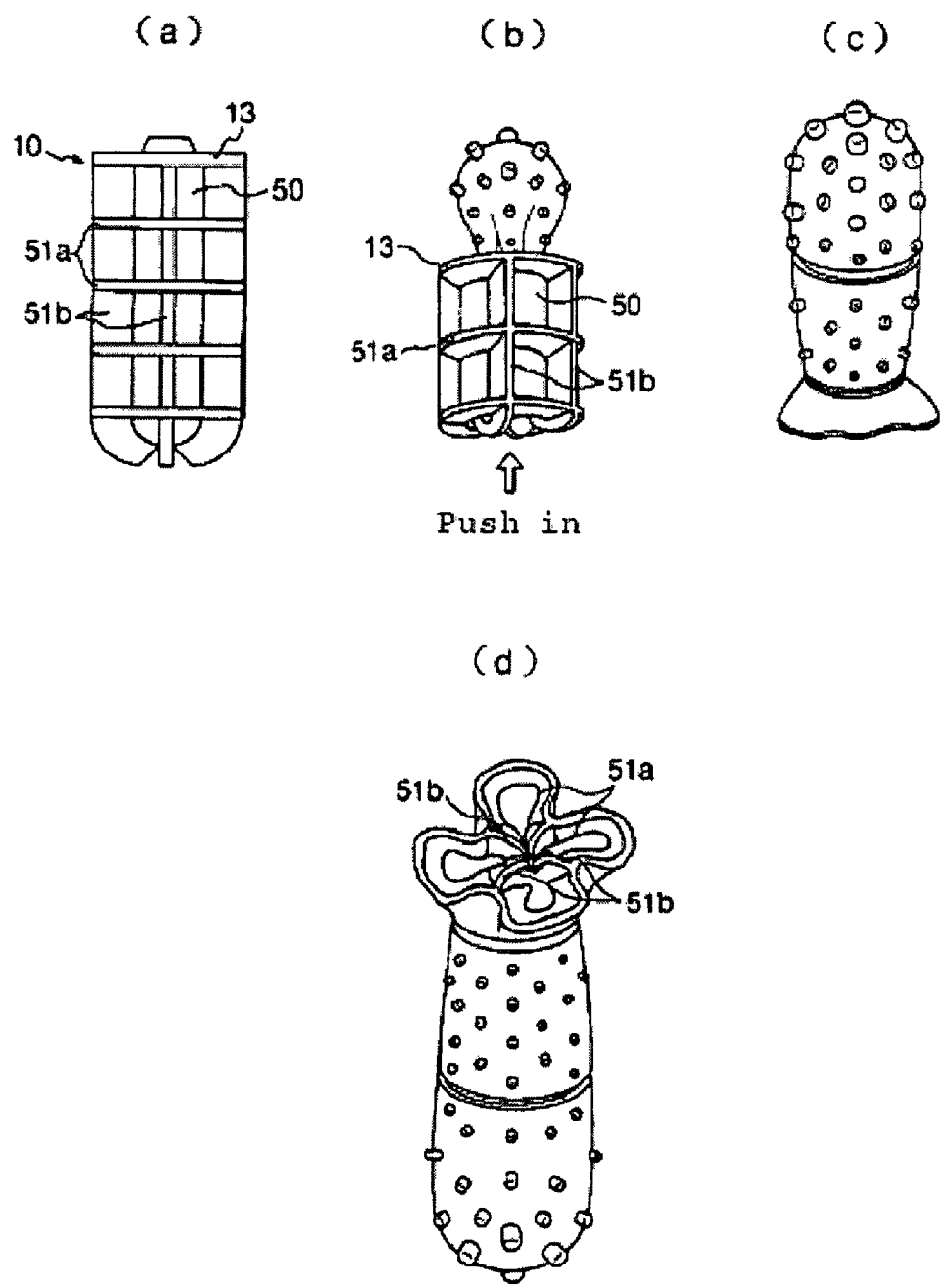
FIGS. 8(a) to 8(d) are explanatory diagrams showing a modification procedure of a sperm collecting apparatus according to a modified embodiment of the present invention.

The lotion leakage prevention structure using the inner cap like the embodiment shown in FIG. 6 can be applied to the embodiment shown in FIG. 8. In the embodiment shown in FIG. 8, the flange portion shown in FIG. 7 can be provided in order to prevent pain during a rubbing operation.

Figure 9:
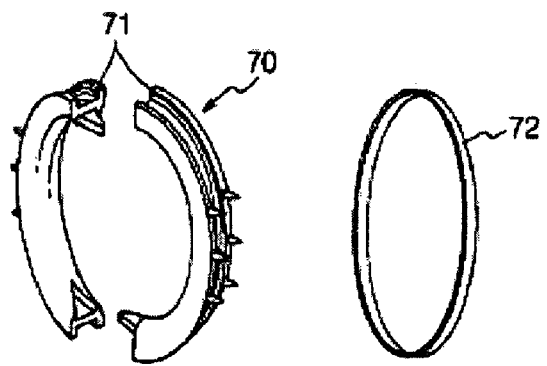
FIGS. 9(a) and 9(b) are an explanatory view of a configuration of a tightening member which is used subsidiarily when the sperm collecting apparatus of the present invention is used and an explanatory view of a using state of the tightening member.
Figure 9:
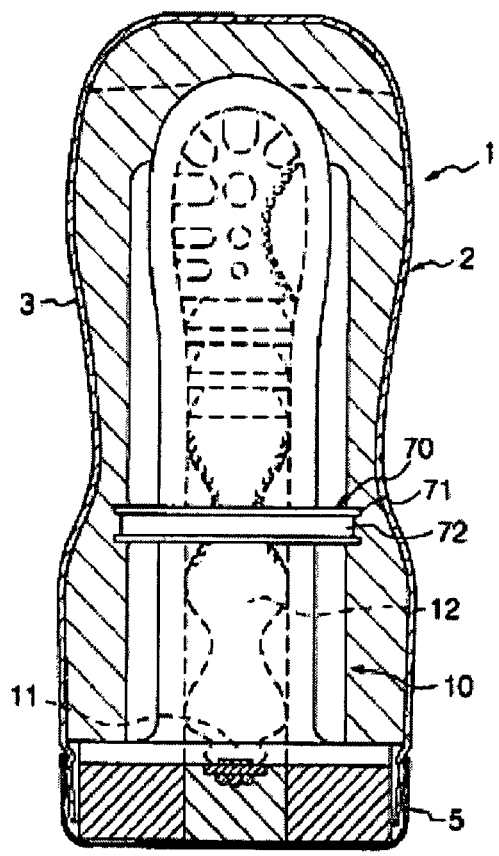

Next, FIGS. 9(a) and 9(b) are an explanatory view of a configuration of a tightening member which is used subsidiarily when the sperm collecting apparatus of the present invention is used and an explanatory view of a using state of the tightening member.

The tightening member 70 includes two arc-shaped clamping pieces 71 made from a relatively hard resin or rubber and an elastic strap 72 wound on an outer peripheral face of the two clamping pieces 71 such as a rubber band, as shown in FIG. 9(a).

As shown in FIG. 9(b), the tightening member 70 put in a state that the elastic strap 72 has been wound on grooves provided on outer peripheral faces of the two holding pieces 71 facing each other is fitted on a proper portion of an outer face of the core member 10. That is, since the two holding pieces 71 can be caused to elastically separate from and approach to each other (is opened and closed) by an elastic force of the elastic strap 72, the tightening member can be elastically fitted on the outer face of the core member 10.

With this configuration, when a user inserts his penis in the insertion room 12 to conduct a rubbing operation, he can apply stimulations to his penis in a state that a tightening force has been increased partially. Therefore, a sperm collecting rate can be remarkably increased.

What is claimed is:

1. A sperm collecting apparatus comprising:
   a container including a cylindrical container main unit having at least one end face in a longitudinal direction and a cap that is attachable to an opening portion of the container main unit to close and open the opening portion;
   a core member made from a gel-like material, which is accommodated in said container and has an insertion room extending from an insertion port at one end face in a longitudinal direction therein;
   wherein said core member includes a core main unit having said insertion port and said insertion room and a plurality of ribs extending from an outer face of the core main unit;
   wherein a plurality of sealed rooms is formed by the outer face of the core main unit, by the plurality of ribs and an inner wall of said container main unit by contacting a plurality of outer end edges of said respective ribs with the inner wall of said container main unit;

wherein said plurality of sealed rooms is arranged in a longitudinal direction of said core member; and wherein said plurality of ribs comprise a plurality of plate-like lateral ribs extending in a direction crossing an axial direction of said core main unit and a plurality of longitudinal ribs extending in a direction parallel to the axial direction of said core main unit and connecting respective said lateral ribs.

2. The sperm collecting apparatus according to claim 1, further comprising an inner cap having a projecting portion which is fitted in the insertion port of said core main unit from the outside to close the insertion port and a supporting face which supports the projecting portion and contacts with one end face of said core main unit in the longitudinal direction.

3. The sperm collecting apparatus according to claim 2, further comprising a space for accumulating lotion is located between the supporting face of said inner cap and one end face of said core main unit in the longitudinal direction.

4. The sperm collecting apparatus according to claim 3, further comprising a flange portion formed on one end face of said core main unit in the longitudinal direction, an outer peripheral edge of the flange portion bulges beyond the opening portion of said container main unit, and the outer peripheral edge of said flange portion is kept in an outwardly-folded state such that the outer peripheral edge of the flange portion covers an end edge of the opening portion of said container main unit.

5. The sperm collecting apparatus according to claim 2, further comprising a flange portion formed on one end face of said core main unit in the longitudinal direction, an outer peripheral edge of the flange portion bulges beyond the opening portion of said container main unit, and the outer peripheral edge of said flange portion is kept in an outwardly-folded state such that the outer peripheral edge of the flange portion covers an end edge of the opening portion of said container main unit.

6. The sperm collecting apparatus according to claim 1, further comprising a flange portion formed on one end face of said core main unit in the longitudinal direction, an outer peripheral edge of the flange portion bulges beyond the opening portion of said container main unit, and the outer peripheral edge of said flange portion is kept in an outwardly-folded state such that the outer peripheral edge of the flange portion covers an end edge of the opening portion of said container main unit.

* * * * *

UNITED STATES PATENT AND TRADEMARK OFFICE
CERTIFICATE OF CORRECTION

PATENT NO. : 7,993,315 B2  
APPLICATION NO. : 11/881750  
DATED : August 9, 2011  
INVENTOR(S) : Tsutomu Matsuura Page 1 of 1

It is certified that error appears in the above-identified patent and that said Letters Patent is hereby corrected as shown below:

Column 15, line 21, claim 4 should refer back to claim 1, which means changing:
"4. The sperm collecting apparatus according to claim 3,"
To --4. The sperm collecting apparatus according to claim 1,--

Column 16, line 15, claim 6 should refer back to claim 3, which means changing:
"6. The sperm collecting apparatus according to claim 1,"
To --6. The sperm collecting apparatus according to claim 3,--

Signed and Sealed this
Twenty-second Day of November, 2011

David J. Kappos
*Director of the United States Patent and Trademark Office*